(12) United States Patent
López Blanco et al.

(10) Patent No.: US 7,560,435 B2
(45) Date of Patent: Jul. 14, 2009

(54) THERAPEUTIC USE OF RIBOSIDE OF 5-AMINOIMIDAZOLE-4-CARBOXAMIDE (ACADESINE)

(75) Inventors: José Manuel López Blanco, Barcelona (ES); Clara Campás Moya, Barcelona (ES); Juan Gil Santano, Barcelona (ES)

(73) Assignee: Advanced In Vitro Cell Technologies, S. A., Barcelona (ES)

( * ) Notice: Subject to any disclaimer, the term of this patent is extended or adjusted under 35 U.S.C. 154(b) by 600 days.

(21) Appl. No.: 10/508,305

(22) PCT Filed: Mar. 20, 2003

(86) PCT No.: PCT/ES03/00130

§ 371 (c)(1), (2), (4) Date: May 11, 2005

(87) PCT Pub. No.: WO03/080076

PCT Pub. Date: Oct. 2, 2003

(65) Prior Publication Data

US 2005/0233987 A1 Oct. 20, 2005

(30) Foreign Application Priority Data

Mar. 21, 2002 (ES) ................................ 200200760

(51) Int. Cl.
*A61K 31/70* (2006.01)
*C07H 19/056* (2006.01)
*C07H 19/207* (2006.01)

(52) U.S. Cl. ...................... 514/43; 536/26.9; 536/28.8

(58) Field of Classification Search ........................ None
See application file for complete search history.

(56) References Cited

U.S. PATENT DOCUMENTS

| | | | | |
|---|---|---|---|---|
| 3,173,848 A | * | 3/1965 | De Zeeuw | 435/87 |
| 3,238,110 A | * | 3/1966 | Konishi et al. | 435/87 |
| 3,355,301 A | | 11/1967 | Huang et al. | 426/537 |
| 3,450,693 A | * | 6/1969 | Izumi et al. | 536/27.6 |
| 4,225,591 A | * | 9/1980 | Marumoto et al. | 514/46 |
| 4,255,565 A | * | 3/1981 | Marumoto et al. | 536/27.61 |
| 4,293,690 A | * | 10/1981 | Sawa et al. | 536/27.61 |
| 4,912,092 A | | 3/1990 | Gruber | 514/45 |
| 5,059,590 A | * | 10/1991 | Ueda et al. | 514/43 |
| 5,082,829 A | * | 1/1992 | Gruber et al. | 514/43 |
| 5,126,361 A | * | 6/1992 | Ueda et al. | 514/400 |
| 5,132,291 A | * | 7/1992 | Gruber | 514/43 |
| 5,187,162 A | | 2/1993 | Marangos et al. | 514/46 |
| 5,200,525 A | * | 4/1993 | Gruber et al. | 548/311.7 |
| 5,236,908 A | | 8/1993 | Gruber et al. | 514/46 |
| 5,658,889 A | * | 8/1997 | Gruber et al. | 514/43 |
| 5,777,100 A | * | 7/1998 | Bullough et al. | 536/26.9 |
| 5,817,640 A | | 10/1998 | Gruber et al. | 514/46 |
| 6,312,662 B1 | * | 11/2001 | Erion et al. | 424/9.1 |
| 6,946,115 B2 | * | 9/2005 | Erion et al. | 424/1.73 |

FOREIGN PATENT DOCUMENTS

| | | |
|---|---|---|
| EP | 0 427 799 B1 | 11/1994 |
| JP | 44/005225 B4 * | 3/1969 |
| WO | WO 93/03734 A1 | 3/1993 |
| WO | WO 01/93873 A1 | 12/2001 |
| WO | WO 01/93874 A1 | 12/2001 |
| WO | WO 01/97816 A1 | 12/2001 |
| WO | WO 02/09726 A1 | 2/2002 |

OTHER PUBLICATIONS

Ulrich et al., "Conformational Restraint Is a Critical Determinant of Unnatural Nucleotide Recognition by Protein Kinases," Bioorganic & Medicinal Chemistry Letters, 12(21), 3223-3227 (Nov. 2, 2002).*
Sigma Biochemicals and Reagents for Life Science Research Catalog, Sigma-Aldrich, St. Louis, MO, 2000-2001 edition, see p. 100, bottom of col. 1 to middle of col. 2.*
Campás et al., "Acadesine Activates AMPK and Induces Apoptosis in B-cell Chronic Lymphocytic Leukemia Cells but Not in T Lymphocytes," Blood, 101(9), 3674-3680 (May 1, 2003); published on-line on Jan. 9, 2003.*
Townsend, L. B., "Imidazole Nucleosides and Nucleotides," Chemical Reviews, 67(5), 533-563 (May 1967).*
Mauser et al., "Influence of Ribose, Adenosine, and 'AICAR' on the Rate of Myocardial Adenosine Triphosphate Synthesis During Reperfusion After Coronary Artery Occlusion in the Dog," Circulation Research, 56, 220-230 (1985).*
Campas et al., "Acadesine Induces Apoptosis in B Cells for Mantle Cell Lymphoma and Splenic Marginal Zone Lymphoma," Leukemia, 19, 292-294 (2005): published on-line Nov. 18, 2004; copy supplied by applicant.*
Matsuda, A. et al., "The Design, Synthesis and Antileukemic Activity of 5-Alkynyl-1-β-D-ribofuranosylimidazole-4-carboxamides" Chem. Pharm. Bull., 1998, vol. 36(7), 2730-2733.

(Continued)

*Primary Examiner*—Shaojia Anna Jiang
*Assistant Examiner*—Lawrence E Crane
(74) *Attorney, Agent, or Firm*—Morgan & Finnegan, L.L.P.

(57) ABSTRACT

The present disclosure relates to a method of treatment of a human patient suffering from a B-cell lymphoproliferative disorders such as B-cell chronic lymphocytic leukemia (B-CLL), splenic marginal zone lymphoma (SMZL), mantle cell lymphoma (MCL), follicular lymphoma (FL), lymphoplasmacytic lymphoma (LPL), and Waldenström syndrome (WS), by the administration of a therapeutically effective amount of 5-aminoimidazole-4-carboxamide riboside (acadesine) or its precursors (eg. its mono-, di- and tri-5'-phosphates). This makes acadesine and its bioprecursors (eg. its mono-, di- and tri-5'-phosphates) useful as therapeutic agents for B-cell lymphoproliferative disorders in humans. The surprising feature that T cells are virtually not affected means that the side effect (immunosuppression) is minor, what represents a therapeutical advantage of acadesine over cladribine, fludarabine and other nucleosides known in the art.

10 Claims, 6 Drawing Sheets

OTHER PUBLICATIONS

Montgomery, J. A. et al., "1-Glycosyl Derivatives of 5-Aminoimidazole-4-carboxamide" *J. Med. Chem.*, 1972, vol. 15(12), 1334-1336.

Witkowski, J. T. et al., "Design, Synthesis, and Broad Spectrum Antiviral Activity of 1-β- Ribofuranosyl-1,2,4-triazole-3-carboxamide and Related Nucleosides" *J. Med. Chem.*, 1972, vol. 15(11), 1150-1153.

Meisse, D. et al., "Sustained activation of AMP-activated protein kinase induces c-Jun N-terminal kinase activation and apoptosis in liver cells" *FEBS Lett.*, 2002, vol. 526, 38-42.

Campás, C. et al., "Acadesine activates AMPK and induces apoptosis in B-cell chronic lymphocytic leukemia cells but not in T lymphocytes" *Blood*, 2003, vol. 101(9), 3674-3680.

Gloria Cristalli, et al., "Adenosine deaminase inhibitors: structure-activity relationships in 1-deazaadenosine and erythro-9-(2-hydroxy-3-nonyl) adenine analogues," *Drug Development Research*, 1993, vol. 28(3), 253-58.

Taisun Ha, et al., "5-Aminoimidazole-4-carboxamide ribotide (AICAR) and its metabolites: metabolic and cytotoxic effects and accumulation during methrotexate treatment," *J. Nutr. Biochem.*, 1994, vol. 5(11), 522-28.

D.T. Mangano, "Effects of acadesine on myocardial infarction, stroke, and death following surgery. A meta-analysis of the 5 international randomized trials. The Multicenter Study of Perioperative Ischemia (McSPI) Research Group," *Journal of the American Medical Association*, 1997, vol. 277(4), 325-32.

B. Bellosillo, et al., "Aspirin and Salicylate Induce Apoptosis and Activation of Caspases in B-Cell Chronic Lymphocytic Leukemia Cells," *Blood*, 1998, vol. 92(4), 1406-14.

\* cited by examiner

THERAPEUTIC USE OF RIBOSIDE OF 5-AMINOIMIDAZOLE-4-CARBOXAMIDE (ACADESINE)

The present application is a national stage entry under 35 U.S.C. §371 of International Application No. PCT/ES03/00130 filed Mar. 20, 2003.

The invention relates to the use of acadesine or acadesine precursors for the treatment of certain types of leukemia and lymphoma in humans.

BACKGROUND ART

Leukemia is a cancer of the blood-forming tissues characterized by a large increase in the numbers of white blood cells (leukocytes) in the circulation, bone marrow or other tissues. A number of different leukemias are classified according to the course of the disease and the predominant type of white blood cell involved. Leukemias are defined as either acute or chronic and as either myelogenous (from bone marrow) or lymphocytic (involving lymphocytes). These characteristics are used to designate almost all cases of leukemia as one of the following four types: acute myelogenous, acute lymphocytic, chronic myelogenous, and chronic lymphocytic leukemia. The two primary types of lymphocytes are B lymphocytes and T lymphocytes, or B cells and T cells.

B-cell chronic lymphocytic leukemia (B-CLL) is characterized by the accumulation of long-lived B lymphocytes. Most of the circulating cells appear to be non-dividing and the clonal excess of B cells is mainly caused by defects that prevent programmed cell death rather than by alterations in cell cycle regulation. Glucocorticoids and other chemotherapeutic agents used clinically, including the nucleoside analogues cladribine (2-chloro-2'-deoxyadenosine) and fludarabine (9-β-D-arabino-2-fluoroadenine, used in the form of 5'-monophosphate), induce apoptosis (also called programmed cell death) in B-CLL lymphocytes, suggesting that apoptosis is the mechanism of their therapeutic action. Thus, fludarabine and other nucleosides are highly effective in the treatment of B-CLL, either alone or in combination with other agents. However, these nucleosides induce apoptosis of T cells. This induction represents an important adverse side-effect because it leads to immunosuppression.

B-cell chronic lymphocytic leukemia (B-CLL) is a particular case of a wider group of conditions that are usually referred as B-cell lymphoproliferative disorders, i.e. disorders and/or diseases related to an abnormal increase in B-cell number or function. Besides B-CLL, this group of conditions include, among others, splenic marginal zone lymphoma (SMZL), mantle cell lymphoma (MCL), follicular lymphoma (FL), lymphoplasmacytic lymphoma (LPL), and Waldenström syndrome (WS). What is mentioned above illustrates that there is a need of new therapeutical agents for the treatment of B-cell lymphoproliferative disorders, and in particular of B-cell chronic lymphocytic leukemia (B-CLL).

Acadesine, which is also named 5-amino-1-β-D-ribofuranosyl-1H-imidazole-4-carboxamide, 5-aminoimidazole-4-carboxamide riboside, AICA riboside and AICAR, is a natural substance with CAS RN 2627-69-2 and with the following formula, where the numbering of hydroxyl groups is shown.

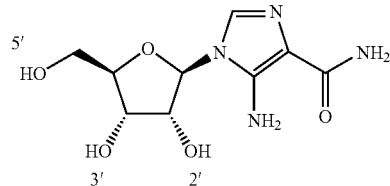

Acadesine 5'-monophospate, which is also named AICA ribotide and ZMP, has CAS RN 3031-94-5 and it is a natural occurring active metabolite of acadesine. Clinical studies in patients undergoing coronary artery bypass graft surgery demonstrate that treatment with acadesine before and during surgery can reduce early cardiac death and myocardial infarction (cf. e.g.: D. T. Mangano, *Journal American Medical Association* 1997, vol. 277, pp. 325-332). Phase III trials have been carried out with acadesine, indicating that it is safe when administered orally and intravenously. There are patents granted and/or patent applications published which relate to the use of acadesine for: preventing tissue damage due to decreased blood flow (cf. U.S. Pat. No. 4,912,092, U.S. Pat. No. 5,817,640); treating neurodegenerative conditions (cf. U.S. Pat. No. 5,187,162); preventing injury to the central nervous system (cf. U.S. Pat. No. 5,236,908); treating obesity (cf. WO 0193873 A1); treating type 2 diabetes (cf. WO 0197816 A1) and treating conditions associated with insulin resistance (cf. WO 0209726 A1). There are patents granted and/or patent applications published which relate to the use of acadesine 5'-monophosphate as flavouring material (cf. U.S. Pat. No. 3,355,301), anticholestermic/antihyperlipemic agent (cf. WO 9303734 A1), antiobesity agent (cf. WO 0193874 A1) and antidiabetic agent (cf. WO 0197816 A1). But nothing is mentioned or suggested in the art related to the use of acadesine, acadesine 5'-monophosphate or any of their prodrugs for treating leukemia and lymphoma.

It is known that acadesine is an apoptosis inhibitor of several cells. Thus, for instance, it is known that acadesine inhibits glucocorticoid-induced apoptosis in quiescent thymocytes, that acadesine inhibits apoptosis caused by serum deprivation in fibroblasts overproducing fructose 2,6-bisphosphate, and that acadesine inhibits ceramide-induced apoptosis in primary astrocytes. Therefore, should acadesine have any effect on lymphocytes apoptosis, acadesine would be expected to be an inhibitor of it.

SUMMARY OF THE INVENTION

Surprisingly, the inventors have found that acadesine induces apoptosis in B cells of samples from patients with some B-cell lymphoproliferative disorders, whereas T cells are virtually unaffected. These unexpected results make acadesine and bioprecursors thereof useful as therapeutic agents for B-cell lymphoproliferative disorders, i.e. disorders and/or diseases related to an abnormal increase in B-cell number or function, which include, among others, the following: B-cell chronic lymphocytic leukemia (B-CLL), splenic marginal zone lymphoma (SMZL), mantle cell lymphoma (MCL), follicular lymphoma (FL), lymphoplasmacytic lymphoma (LPL), and Waldenström syndrome (WS).

The differential effect of acadesine on B and T lymphocytes is an important advantage of the invention, because it means that the side effect of immunosuppression is minor when using acadesine as anti-leukemia agent. In particular, this represents a therapeutical advantage over the use of fludarabine or other nucleosides known in the art.

Another important advantage of the invention is the selectivity and the concentration of acadesine necessary to induce apoptosis. The inventors have studied the effects of acadesine in different cell lines including Jurkat (T cell line), JVM-2, MCF-7 (breast cancer line), 293, Hela (cervix cancer line) and HUH7 (liver cancer line), and it has been found that all these cell lines were less sensitive to acadesine than B-CLL cells. This means that the possible side effects coming from damaging other cellular types are minor when using acadesine as a therapeutical agent. Besides, acadesine is well tolerated by healthy individuals when given intravenously, achieving concentrations in plasma (200 µM) in the range of those producing apoptosis in cells from B-CLL patients.

In order to improve the therapeutic potential of acadesine (e.g. its gastrointestinal absorption) some acadesine bioprecursors have been disclosed (cf. U.S. Pat. No. 5,817,640, EP 0 427 799 B1 and references therein) which, when introduced in the body, metabolize into acadesine or an active form thereof. By acadesine bioprecursors it is here meant compounds of formula (I) wherein —$R_2$, —$R_3$ and —$R_5$ are radicals independently selected from the group consisting of —H (acadesine itself corresponding to the selection —$R_2$=—$R_3$=—$R_5$=—H); —PO(OH)$_2$; —PO(OH)—O—PO(OH)$_2$; —PO(OH)—O—PO(OH)—O—PO(OH)$_2$; —CO—R' and —CO—OR'; R' being a hydrocarbyl radical up to twelve carbon atoms, which may be aliphatic (including alkyl, alkenyl, and alkynyl groups and groups which have a mixture of saturated and unsaturated bonds), alicyclic (carbocyclic), aryl (aromatic) or a combination thereof; wherein —R' may be a radical from a straight-chain, a branched-chain, a cycle or a combination thereof; —R' may have one or more hydrogen atoms substituted by one or more halogen atoms, and/or by one or more ($C_1$-$C_4$)-alkyl groups; —R' may have one or more $CH_2$ groups substituted by one or more NH, O and/or S groups; and —R' may have one or more CH groups substituted by one or more N atoms. In this context a halogen atom means an atom of F, Cl, Br or I.

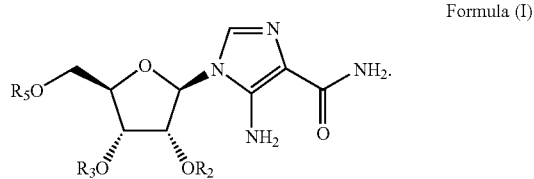

Formula (I)

The present invention relates to a method of treatment of a human suffering from a B-cell lymphoproliferative disorder, comprising administering to said patient a therapeutically effective amount of acadesine or an acadesine bioprecursor of formula (I), as defined above, or of a pharmaceutically acceptable solvate or addition salt thereof, together with pharmaceutically acceptable diluents or carriers. Preferably, compounds of formula (I) are administered orally or parenterally (more preferably, intravenously). In particular embodiments of the method, the B-cell lymphoproliferative disorders are B-CLL, SMZL, MCL, FL, LPL, WS and B-cell lymphoproliferative disorders without a specific diagnosis.

An aspect of the present invention refers to the use of a compound of formula (I) as defined above, which is acadesine or an acadesine bioprecursor, or a pharmaceutically acceptable solvate or addition salt thereof, for the preparation of a medicament for the treatment of humans suffering from B-cell lymphoproliferative disorders. In particular embodiments, the B-cell lymphoproliferative disorders are B-CLL, SMZL, MCL, FL, LPL, WS and B-cell lymphoproliferative disorders without a specific diagnosis, respectively. In a preferred embodiment, the compound of formula (I) has —$R_2$, —$R_3$ and —$R_5$ independently selected from the group consisting of: —H; —PO(OH)$_2$; —PO(OH)—O—PO(OH)$_2$ and —PO(OH)—O—PO(OH)—O—PO(OH)$_2$. In a more preferred embodiment, the compound of formula (I) is selected from the group consisting of acadesine and acadesine 5'-monophosphate. In a still more preferred embodiment, the compound of formula (I) is acadesine.

Throughout the description and claims the word "comprise" and variations of the word, such as "comprising", is not intended to exclude other technical features, additives, components, or steps. The content of the application from which priority is claimed, as well as the contents of the abstracts of the priority application and of the present application, are incorporated herein as reference. The following detailed description and drawings are provided by way of illustration, and they are not intended to be limiting of the present invention.

DETAILED DESCRIPTION OF PARTICULAR EMBODIMENTS

Patients and Cell Isolation

Forty-six patients with B-CLL, seven patients with SMZL, two patients with lymphoproliferative disorder without a specific diagnosis, and four healthy donors were studied. All patients were diagnosed according to standard clinical and laboratory criteria. Written informed consent was obtained from all patients. Mononuclear cells from peripheral blood samples were isolated by centrifugation on a Ficoll/Hypaque (Seromed, Berlin, Germany) gradient and cryopreserved in liquid nitrogen in the presence of 10% dimethyl sulfoxide (DMSO).

Cell Culture

Lymphocytes were cultured immediately after thawing at a concentration of 2 to $5\times10^6$ cells/ml in RPMI 1640 culture medium (Biological Industries, Beit Haemek, Israel) supplemented with 10% heat-inactivated fetal calf serum (Gibco-BRL, Paisley, GB), 1% glutamine, and 1% penicillin-streptomycin at 37° C. in a humidified atmosphere containing 5% carbon dioxide.

Analysis of Apoptosis by Flow Cytometry

Apoptosis was measured by annexin V binding. Exposure of phosphatidylserine was quantified by surface annexin V staining as previously described (cf. B. Bellosillo et al., *Blood* 1998, vol. 92, pp. 1406-1414). To analyze apoptosis in T cells from the samples, 500,000 cells were incubated for 24 h with the indicated factors. Cells were then washed in phosphate-buffered saline (PBS) solution, and incubated in 50 µl of annexin binding buffer with APC-conjugated anti-CD3 and PE-conjugated anti-CD19 for 10 minutes in the dark. Cells were then diluted with annexin binding buffer to a volume of 250 µl and incubated with 0.5 µl of annexin V-FITC for 15 minutes in the dark. 250 µl of annexin binding buffer and 5 µl of PI were added just before flow cytometric analysis. Data were analyzed using Cell Quest software.

Figure 1:
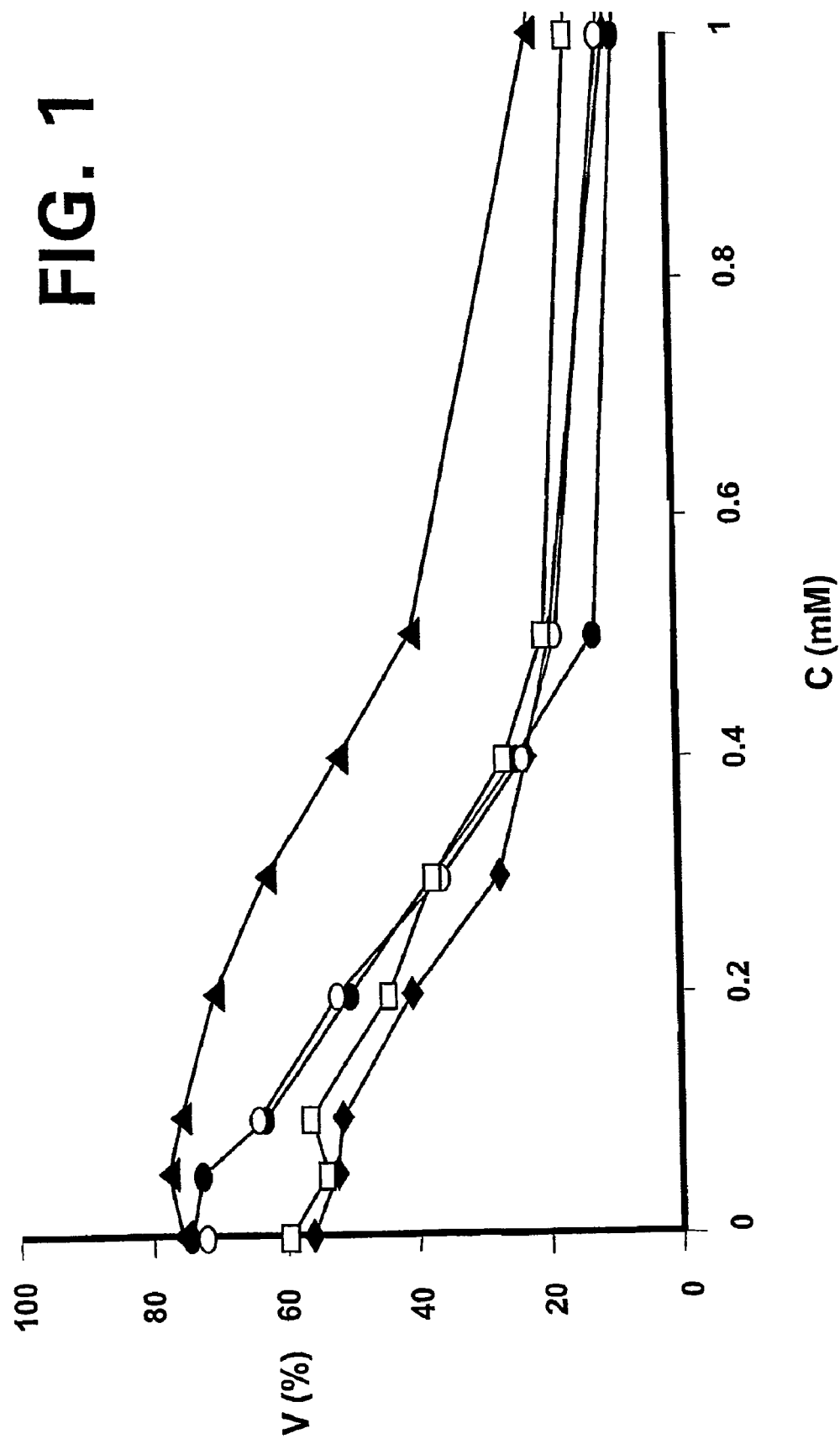
FIG. 1 illustrates the cytotoxic effect of acadesine on cells from B-CLL patients, by showing the viability percentage of B-CLL cells from 5 patients in response to 24 h-incubation with various doses of acadesine expressed in mM.

Acadesine Induces Apoptosis in Cells from Patients with B-CLL, SMZL and Lymphoproliferative Disorders without a Specific Diagnosis The effect of several doses of acadesine, ranging from 50 µM to 1 mM, on the viability of B-CLL cells, was studied. Unexpectedly, acadesine induced apoptosis in a dose-dependent manner, as illustrated in FIG. 1. Cells from 5 patients were incubated for 24 h with various doses of acadesine as indicated. The $EC_{50}$ was 380±60 µM (n=5) for B-CLL cells.

Figure 2:
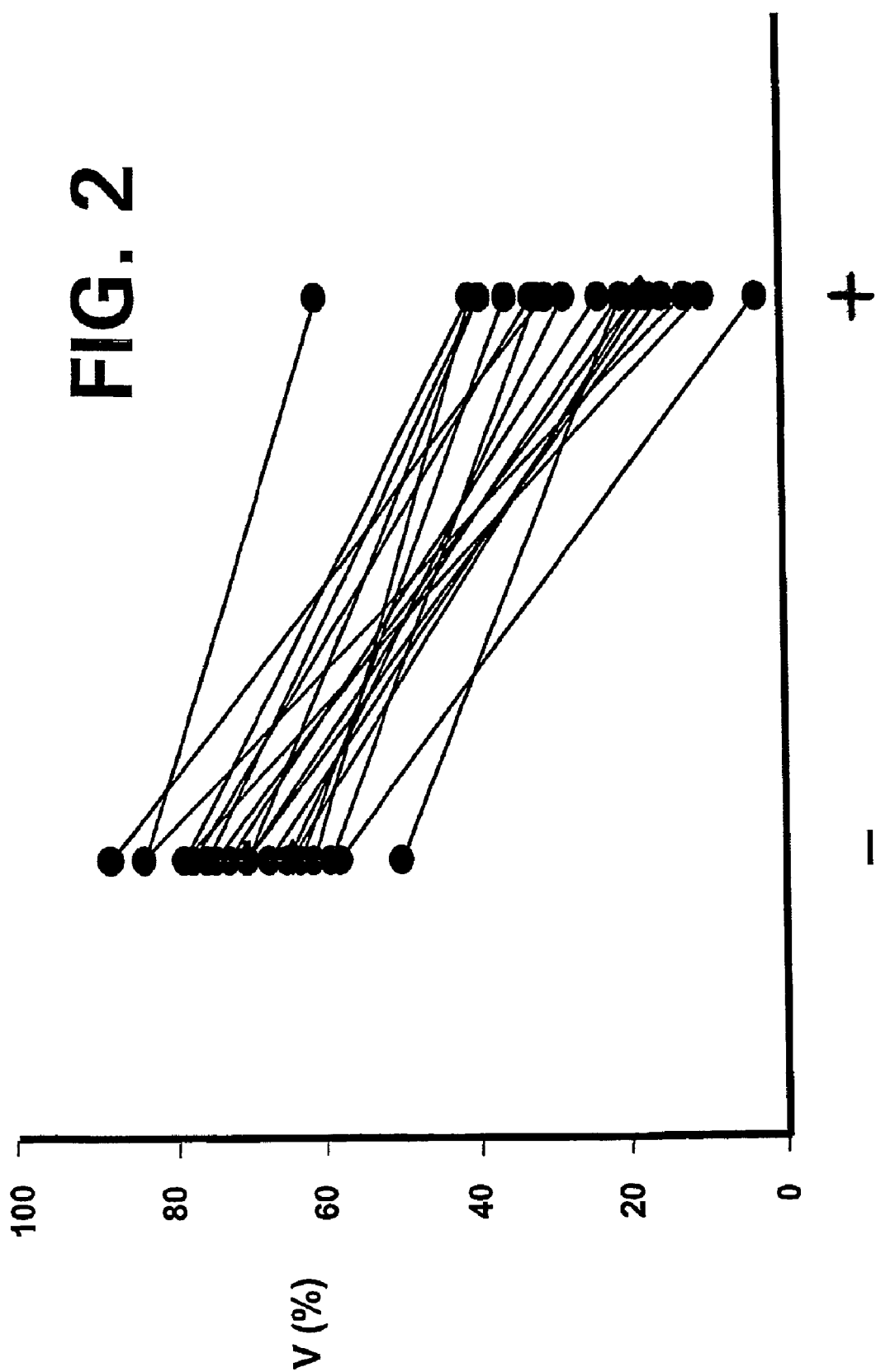
FIG. 2 illustrates the cytotoxic effect of acadesine on cells from B-CLL patients, by showing the effect of 24 h-incubation with (+) or without (−) 0.5 mM acadesine on the viability percentage of B-CLL cells from 20 patients. Viability (V) was measured by analysis of phophatidylserine exposure and PI uptake, and it is expressed as the percentage of non apoptotic cells.

Cells from 46 patients were incubated for 24 h with (+) or without (−) 0.5 mM acadesine. Viability (V) was measured by analysis of phosphatidylserine exposure and PI uptake, and it is expressed as the percentage of non apoptotic cells. All the patients were sensitive to acadesine and the viability decreased from 67±11% to 26±14% (n=46). FIG. 2. shows results from 20 patients.

Figure 5:
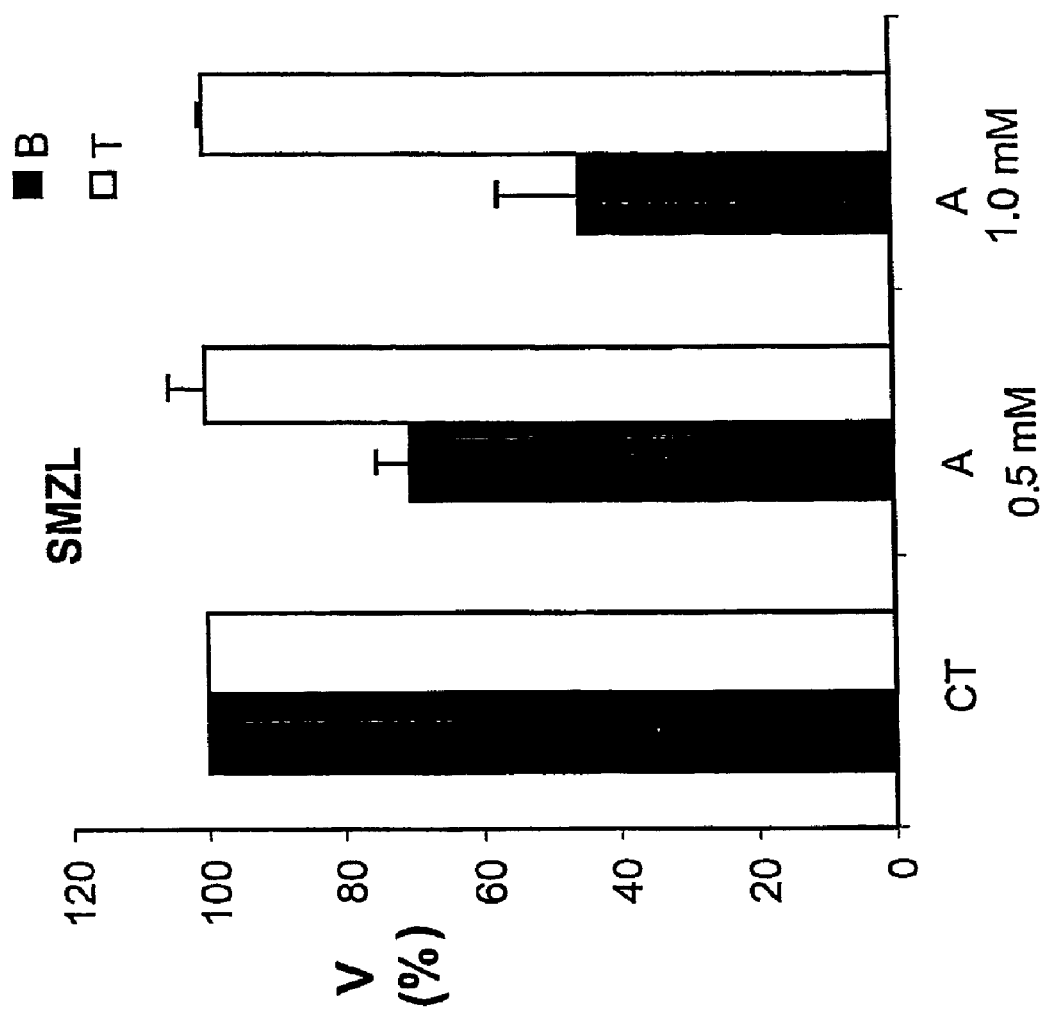
FIG. 5 shows the results of seven samples from SMZL patients. Cells were treated with (A=acadesine, 0.5 mM and 1.0 mM) or without (CT=control) acadesine for 24 hours. Viability (V, %) was analyzed by flow cytometry (annexin V binding). Black and empty bars correspond to B cells and T cells, respectively.
Figure 6:
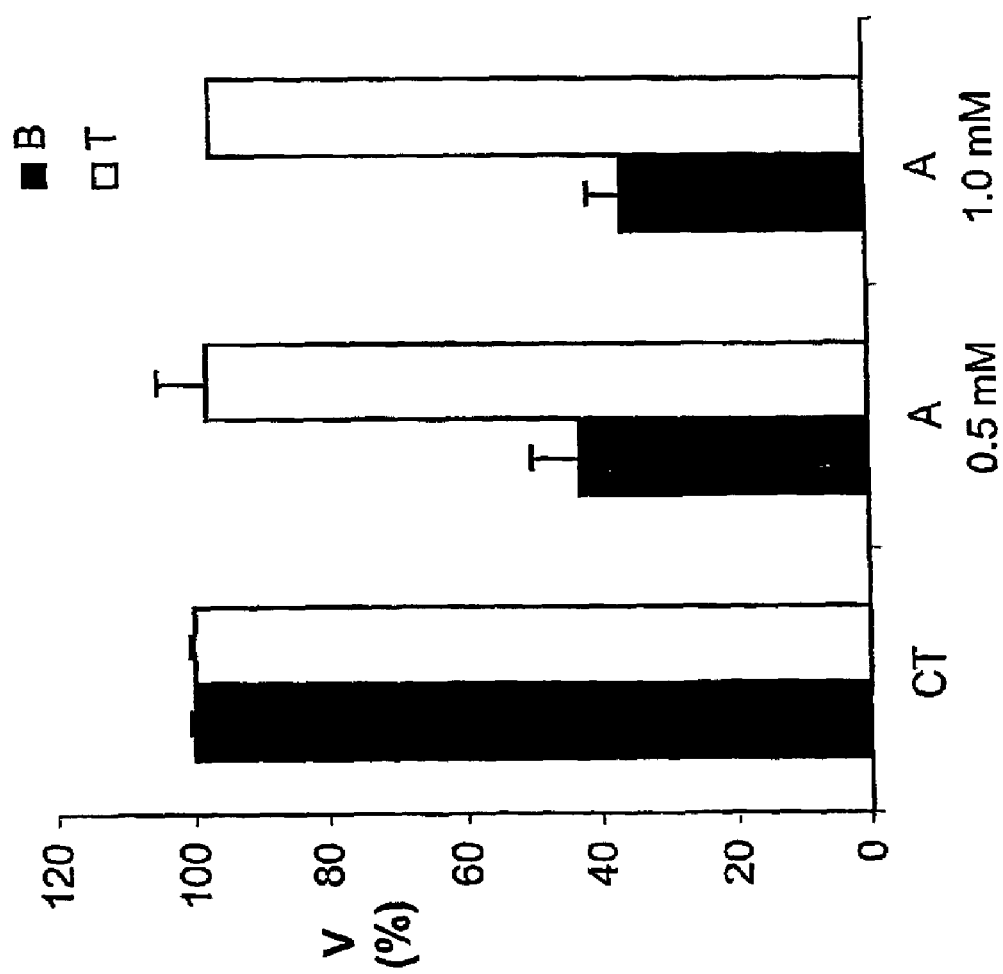
FIG. 6 shows the results of two samples from patients suffering lymphoproliferative disorders without a specific diagnosis. Cells were treated with (A=acadesine, 0.5 mM and 1.0 mM) or without (CT=control) acadesine for 24 hours. Viability (V, %) was analyzed by flow cytometry (annexin V binding). Black and empty bars correspond to B cells and T cells, respectively.

Cells from seven patients with SMZL and two patients with lymphoproliferative disorder without a specific diagnosis were incubated for 24 h with (A) or without (CT) 0.5 mM and 1.0 mM acadesine (cf. FIGS. 5 & 6). Viability (V) was measured by analysis of phosphatidylserine exposure and PI uptake, and it is expressed as the percentage of non apoptotic cells.

Differential Effect of Acadesine on B and T Cells

Figure 3:
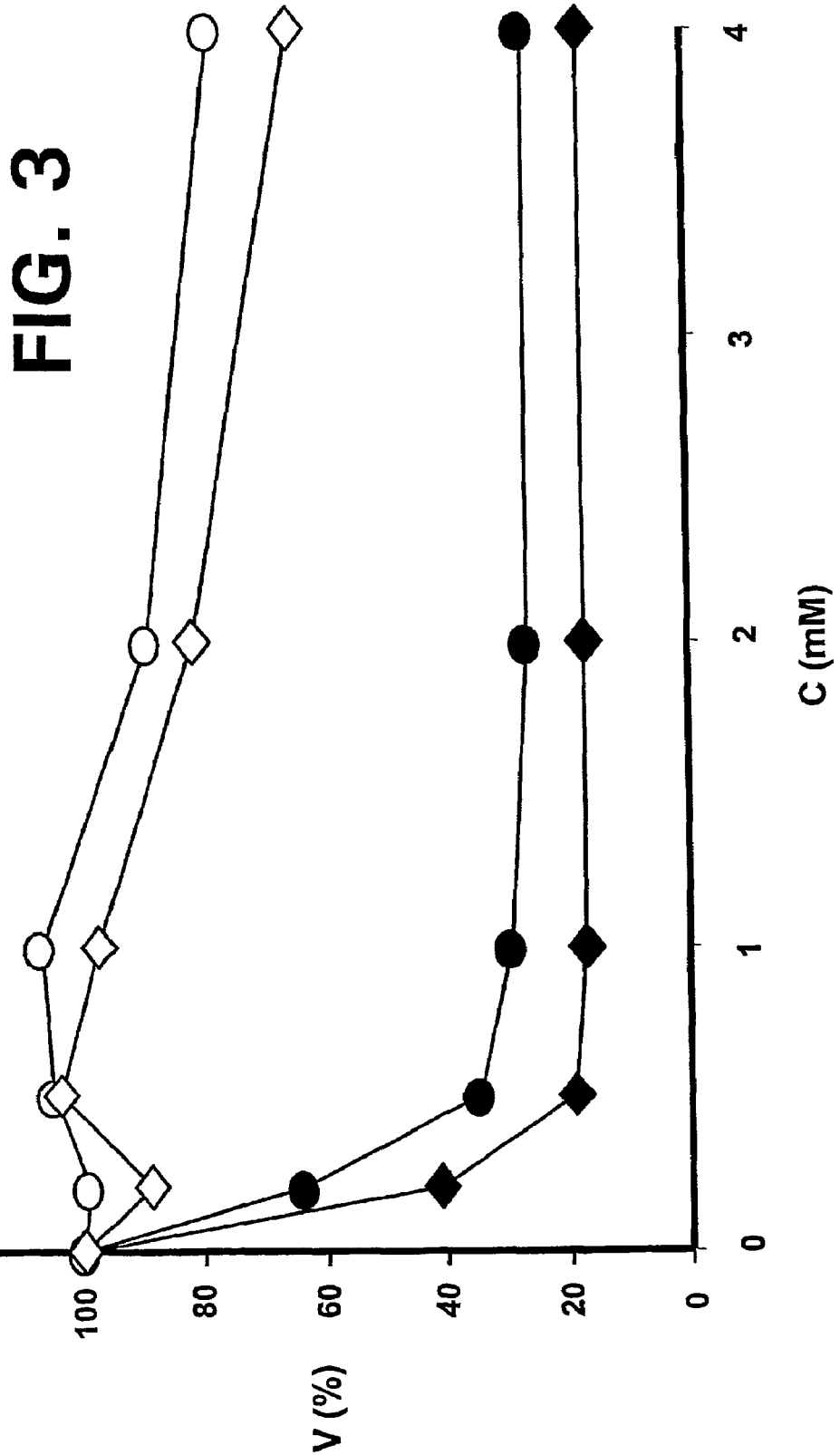
FIG. 3 illustrates the differential cytotoxic effect of acadesine on B cells (full circles and diamonds) and T cells (empty circles and diamonds) from two B-CLL patients in response to 24 h-incubation with various doses of acadesine expressed in mM. Viability (V) was measured as non apoptotic CD3+/CD19− T cells or CD3−/CD19+ B cells, and it is expressed as the percentage of the viability of the non treated cells.

To analyze whether the induction of apoptosis in B-CLL patients was selective to B cells, we counted the apoptotic T cells (CD3 positive cells) in four B-CLL blood samples treated for 24 h with several doses of acadesine. FIG. 3 shows the results corresponding to two representative patients. Viability (V) was measured as non apoptotic CD3+/CD19− T cells (empty symbols) or CD3−/CD19+B cells (full symbols), and it is expressed as the percentage of the viability of non treated cells. T cells from B-CLL samples were resistant to acadesine-induced apoptosis at doses up to 1 mM. Higher concentrations of acadesine (2-4 mM) only slightly affected the viability of T cells.

Figure 4:
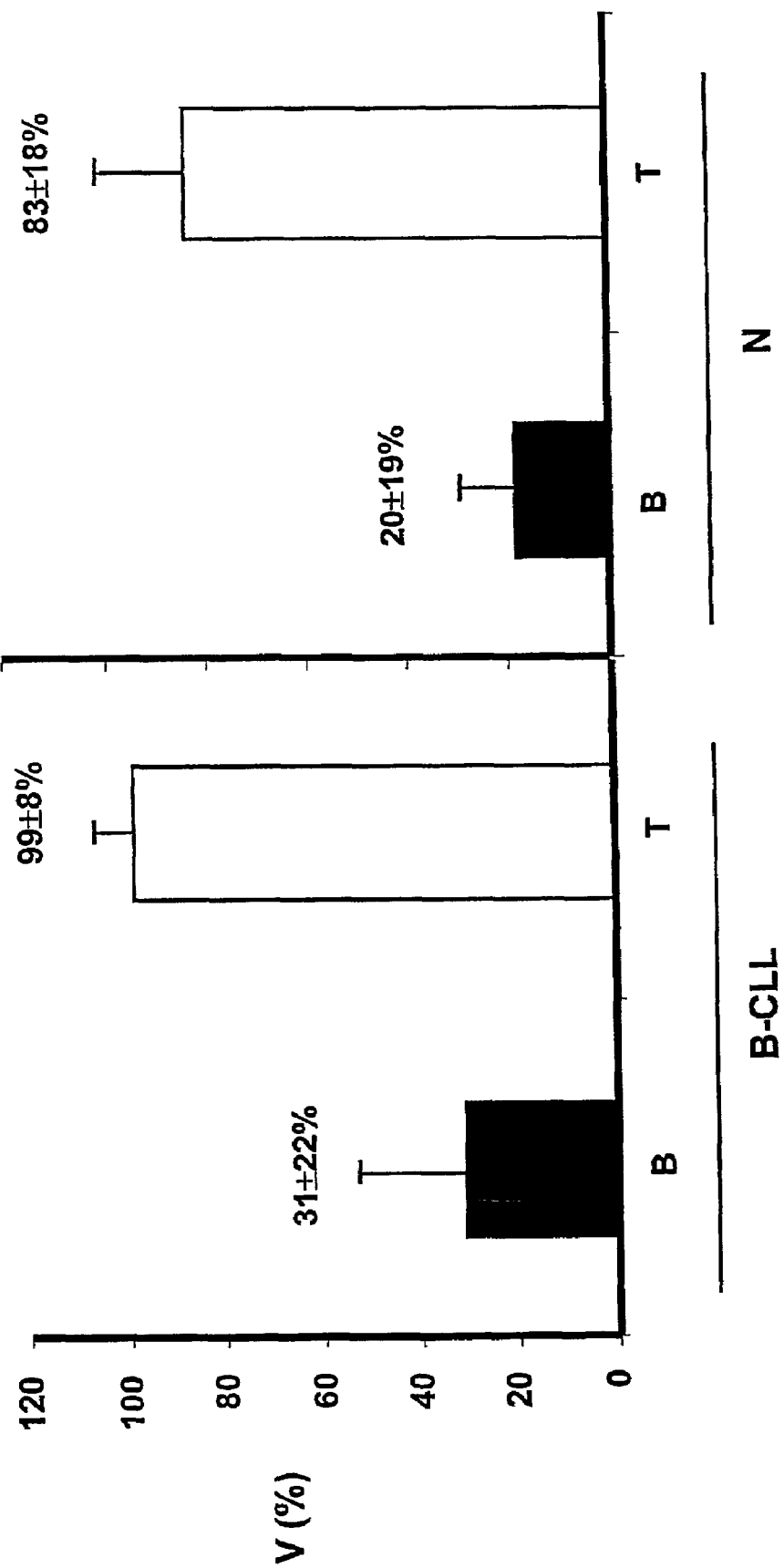
FIG. 4 shows a comparison between the induction of apoptosis in B cells (black bars) and T cells from 18 B-CLL patients (B-CLL) and 4 healthy donors (N) after incubation with 0.5 mM acadesine for 24 h. Viability is expressed as the mean value ± standard deviation.

FIG. 4 shows a comparison between the induction of apoptosis in B and T cells from B-CLL patients and healthy donors (N). Cells from 18 patients and 4 healthy donors were incubated with 0.5 mM of acadesine for 24 h. Viability is expressed as the mean value ± standard deviation. It was observed that viability was markedly reduced in B cells, but not in T cells. These results indicate that B cells are much more sensitive than T cells to acadesine-induced apoptosis.

FIG. 5 and FIG. 6 show a comparison between the acadesine induced-apoptosis in B and T cells, from patients with SMZL and lymphoproliferative disorder without a specific diagnosis. It was observed that viability was markedly reduced in B cells, but not in T cells. These results indicate that B cells are much more sensitive than T cells to acadesine-induced apoptosis.

The invention claimed is:

1. A method of treatment of a human patient suffering from a B-cell lymphoproliferative disorder, comprising administering a therapeutically effective amount of a compound of formula (I), or a pharmaceutically acceptable solvate or addition salt thereof, together with appropriate amounts of pharmaceutically acceptable diluents or carriers; wherein, —$R_2$, —$R_3$ and —$R_5$ are radicals independently selected from the group consisting of —H, PO(OH)$_2$, PO(OH)—O—PO(OH)$_2$, PO(OH)—O—PO(OH)—O—PO(OH)$_2$, CO—R' and CO—OR'; R' being a hydrocarbyl radical up to twelve carbon atoms, which may be aliphatic including alkyl, alkenyl, and alkynyl groups and groups which have a mixture of saturated and unsaturated bonds, alicyclic, aryl or a combination thereof; wherein R' may be a radical from a straight-chain, a branched-chain, a cycle or a combination thereof; —R' may have one or more hydrogen atoms substituted by one or more halogen atoms, and/or by one or more ($C_1$-$C_4$)-alkyl groups; R' may have one or more $CH_2$ groups substituted by one or more NH, O and/or S groups; and R' may have one or more CH groups substituted by one or more N atoms

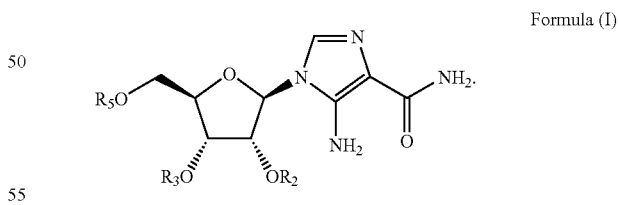

Formula (I)

2. The method according to claim 1, wherein in the compound of formula (I) —$R_2$, —$R_3$ and —$R_5$ are radicals independently selected from the group consisting of H, PO(OH)$_2$, PO(OH)—O—PO(OH)$_2$ and PO(OH)—O—PO(OH)—O—PO(OH)$_2$.

3. The method according to claim 2, wherein in the compound of formula (I) —$R_2$ and —$R_3$ are radicals H, and —$R_5$ is a radical selected from the group consisting of H and —PO(OH)$_2$.

4. The method according to claim 3, wherein in the compound of formula (I) —$R_2$, —$R_3$ and —$R_5$ are radicals H.

5. The method according to any of the claims 3 to 4, wherein the B-cell lymphoproliferative disorder is B-cell chronic lymphocytic leukemia.

6. The method according to any of the claims 1 to 4, wherein the B-cell lymphoproliferative disorder is splenic marginal zone lymphoma.

7. The method according to any of the claims 1 to 4, wherein the B-cell lymphoproliferative disorder is mantle cell lymphoma.

8. The method according to any of the claims 1 to 4, wherein the B-cell lymphoproliferative disorder is follicular lymphoma.

9. The method according to any of the claims 1 to 4, wherein the B-cell lymphoproliferative disorder is lymphoplasmacytic lymphoma.

10. The method according to any of the claims 1 to 4, wherein the B-cell lymphoproliferative disorder is Waldenström syndrome.

* * * * *

UNITED STATES PATENT AND TRADEMARK OFFICE
CERTIFICATE OF CORRECTION

| | | |
|---|---|---|
| PATENT NO. | : 7,560,435 B2 | Page 1 of 1 |
| APPLICATION NO. | : 10/508305 | |
| DATED | : July 14, 2009 | |
| INVENTOR(S) | : Lopez Blanco et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 861 days.

Signed and Sealed this
Eleventh Day of January, 2011

David J. Kappos
*Director of the United States Patent and Trademark Office*